(12) United States Patent
Chen et al.

(10) Patent No.: US 11,779,198 B2
(45) Date of Patent: Oct. 10, 2023

(54) PACKAGE FOR CAPSULE ENDOSCOPE

(71) Applicants: ANKON TECHNOLOGIES CO., LTD, Wuhan (CN); ANX IP HOLDING PTE. LTD., Singapore (SG)

(72) Inventors: Yun Chen, Wuhan (CN); Yunwen Chen, Wuhan (CN); Hao Liu, Wuhan (CN)

(73) Assignees: ANX IP HOLDING PTE. LTD., Wuhan (CN); ANKON TECHNOLOGIES CO., LTD, Singapore (SG)

( * ) Notice: Subject to any disclaimer, the term of this patent is extended or adjusted under 35 U.S.C. 154(b) by 42 days.

(21) Appl. No.: 17/330,311

(22) Filed: May 25, 2021

(65) Prior Publication Data

US 2021/0361148 A1 Nov. 25, 2021

(30) Foreign Application Priority Data

May 25, 2020 (CN) .......................... 202010447653.X (51) Int. Cl.
*A61B 1/00* (2006.01)
*A61B 1/04* (2006.01)
*B65D 75/36* (2006.01)
*B65D 77/04* (2006.01)

(52) U.S. Cl.
CPC .......... *A61B 1/00144* (2013.01); *A61B 1/041* (2013.01); *B65D 75/366* (2013.01); *B65D 77/0446* (2013.01)

(58) Field of Classification Search
CPC .. A61B 1/00144; A61B 1/041; B65D 75/366; B65D 77/0446
USPC ........................................ 206/530, 438, 363
See application file for complete search history.

(56) References Cited

U.S. PATENT DOCUMENTS

| 4,542,825 A | * | 9/1985 | Thomas | ................. | A61B 17/28 |
| | | | | | 206/229 |
| 4,750,619 A | * | 6/1988 | Cohen | .................. | B65D 81/127 |
| | | | | | 206/828 |
| 5,474,179 A | * | 12/1995 | Iosif | ........................ | A61F 5/451 |
| | | | | | 206/521 |
| 5,868,253 A | * | 2/1999 | Krueger | ................ | A61F 2/0095 |
| | | | | | 206/583 |

(Continued)

FOREIGN PATENT DOCUMENTS

CN 101065047 10/2007
CN 101511702 8/2009
(Continued)

*Primary Examiner* — Jacob K Ackun
(74) *Attorney, Agent, or Firm* — Treasure IP Group, LLC (57) ABSTRACT

The present invention discloses a package for a capsule endoscope. The package includes an inner package. The inner package includes a base and a cover arranged above the base. A first end of the cover is connected to a first side of the base and a second end of the cover is connected to a second side of the base in an assembled mode. When the second end of the cover is assembled and connected to the second side of the base, the bottom surface of the cover and the base form an holding slot for holding the capsule endoscope. Through such arrangement, the present invention improves the existing package and avoids a reduction of performance of the capsule endoscope during transportation.

15 Claims, 5 Drawing Sheets

(56) References Cited

U.S. PATENT DOCUMENTS

| | | | | |
|---|---|---|---|---|
| 6,874,629 B1* | 4/2005 | Wortrich | A61B 17/3217 |
| | | | | 206/349 |
| 7,295,226 B1* | 11/2007 | Meron | A61B 1/00144 |
| | | | | 600/114 |
| 7,607,538 B2* | 10/2009 | Silvenis | A45C 11/24 |
| | | | | 206/530 |
| 7,694,824 B2* | 4/2010 | Bae | A45D 33/006 |
| | | | | 206/530 |
| 2003/0168370 A1* | 9/2003 | Merboth | A01N 1/0263 |
| | | | | 206/438 |
| 2008/0039675 A1* | 2/2008 | Segawa | A61B 1/041 |
| | | | | 600/7 |
| 2008/0060952 A1* | 3/2008 | Negron | A61B 1/00057 |
| | | | | 206/210 |
| 2008/0073233 A1 | 3/2008 | Landis | |
| 2008/0257768 A1* | 10/2008 | Uchiyama | A61B 1/041 |
| | | | | 600/101 |
| 2009/0095649 A1* | 4/2009 | Costa | B65D 83/0463 |
| | | | | 206/530 |
| 2010/0300922 A1* | 12/2010 | Gilad | A61B 1/00144 |
| | | | | 206/530 |
| 2012/0080351 A1* | 4/2012 | Takahashi | B65D 25/101 |
| | | | | 206/528 |
| 2022/0409919 A1* | 12/2022 | Ben-Yehuda | A61N 5/0603 |

FOREIGN PATENT DOCUMENTS

| | | |
|---|---|---|
| CN | 102753081 | 10/2012 |
| CN | 107582170 | 1/2018 |
| CN | 109229744 | 1/2019 |
| CN | 305162050 | 5/2019 |
| CN | 209450496 | 10/2019 |
| CN | 110550329 | 12/2019 |
| CN | 209984178 | 1/2020 |

\* cited by examiner

PACKAGE FOR CAPSULE ENDOSCOPE

CROSS-REFERENCE OF RELATED APPLICATIONS

The application claims priority to Chinese Patent Application No. 202010447653.X filed on May 25, 2021, the contents of which are incorporated by reference herein.

FIELD OF INVENTION

The present invention relates to the art of a medical device, and more particularly to a package for a capsule endoscope.

BACKGROUND

Capsule endoscope is a medical device that is swallowed into the digestive tract and takes images therein with a miniature camera for the purpose of examining the digestive tract for diseases. After production, the finished capsule endoscope needs to be packaged and shipped.

Currently, the common package for a capsule endoscope is usually composed of upper and lower rigid shells that are simply closed for protection of the capsule endoscope. The capsule endoscope is placed in the accommodation section between the upper and lower rigid shells. The upper shell has an interference fit with the capsule endoscope to hold the capsule endoscope in place. In the shipping process, a direct squeezing contact between the upper shell and the capsule endoscope easily leads to a great pressure on the capsule endoscope, and the shipping reliability of the capsule endoscope is also greatly reduced.

SUMMARY OF THE INVENTION

The present invention provides a package for a capsule endoscope to improve the existing package and avoid a reduction of performance of the capsule endoscope during transportation.

According to aspects of the present invention, a package for a capsule endoscope is provided. The package comprises an inner package. The inner package comprises a base and a cover arranged above the base. A first end of the cover is connected to a first side of the base and a second end of the cover is connected to a second side of the base in an assembled mode. When the second end of the cover is assembled and connected to the second side of the base, the bottom surface of the cover and the base form an holding slot for holding the capsule endoscope.

In one embodiment, the first end of the cover is pivotally connected to the first side of the base.

In one embodiment, the second end of the cover comprises a first snap hook, and the second side of the base comprises a fitted limit portion. The first snap hook fits with the limit portion to connect the cover to the base by means of snap fit.

In one embodiment, the bottom surface of the cover comprises a soft rubber structure. When the second end of cover is assembled and connected to the second side of the base, the soft rubber structure and the base form the holding slot.

In one embodiment, the soft rubber structure is an arc-shaped structure whose surface shape is adapted to the shape of the outer surface of the capsule endoscope, and the arc-shaped soft rubber structure can form a cylindrical holding slot with the base.

In one embodiment, the inner diameter of the cylindrical holding slot matches the outer diameter of the capsule endoscope.

In one embodiment, the base comprises a base body and a holder fixedly connected to the base body. When the second end of cover is assembled and connected to the second side of the base, the soft rubber structure and the holder form the holding slot.

In one embodiment, the length of the holding slot is not greater than the length of the middle enclosure of the capsule endoscope.

In one embodiment, the package further comprises a sealing structure. The sealing structure comprises a blister case and a dialysis paper. The surface of the blister case is recessed to form a first holding chamber. The inner package can be fixed in the first holding chamber. The dialysis paper is seamlessly connected to the upper surface edge of the blister case to seal the first holding chamber.

In one embodiment, the package further comprises an outer package. The outer package comprises an upper cover and a lower cover that are detachably connected, and the upper cover and the lower cover form a second holding chamber. The sealing structure is fixed in the second holding chamber.

The advantages of the present disclosure comprises: By providing a cover connected to the base, one end of the cover being openably connected to the base, and a holding slot being formed between the cover and the base to hold the capsule endoscope, the reliability of transporting the capsule endoscope is enhanced.

DETAILED DESCRIPTION

In order to make the purpose, technical solutions, and advantages of the present invention clearer, the technical solutions of the present invention can be described clearly and completely in conjunction with the specific embodiments of the present invention and the accompanying drawings. Obviously, the described embodiments are only a part of the embodiments of the present invention, rather than all of the embodiments. Based on the embodiments of the present invention, all other embodiments obtained by those of ordinary skill in the art without creative work shall fall within the protection scope of the present invention.

The following describes the embodiments of the present invention in detail. Examples of the embodiments are shown in the accompanying drawings, in which the same or similar reference numerals indicate the same or similar elements or elements with the same or similar functions. The following embodiments described with reference to the accompanying drawings are exemplary, and are only used to explain the present invention, but should not be understood as limiting the present invention.

For the convenience of description, the terms representing spatial relative positions such as "upper", "lower", "inner", "outer", etc. are used herein to describe the positional relationship of one unit or feature to another unit or feature as shown in the accompanying drawings. These terms may include different orientations of the device in use or operation other than the orientations shown in the accompanying drawings. For example, if the device shown in the accompanying drawings is turned over, the units or features that are described as "Below" or "Above" other units or features can be located "Below" or "Above" other units or features. Thus, the exemplary term "Below" can encompass two orientations of "Below" and "Above".

Referring to FIGS. 1~10, a package for a capsule endoscope is provided, comprising an inner package 2. The inner package 2 comprises a base 21 and a cover 22 arranged above the base 21. A first end of the cover 22 is connected to a first side of the base 21 and a second end of the cover 22 is connected to a second side of the base 21 in an assembled mode. When the second end of the cover 22 is assembled and connected to the second side of the base 21, the bottom surface of the cover 22 and the base 21 form an holding slot 25 for holding the capsule endoscope 8.

Figure 1:
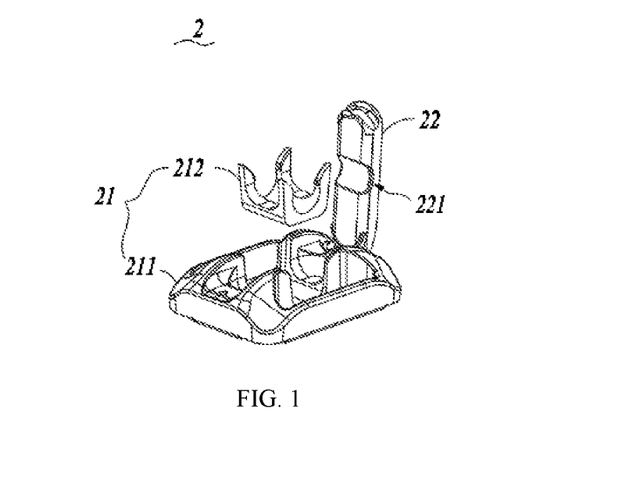
FIG. 1 is an exploded view of an embodiment illustrating an inner package in accordance with the present invention.
Figure 2:
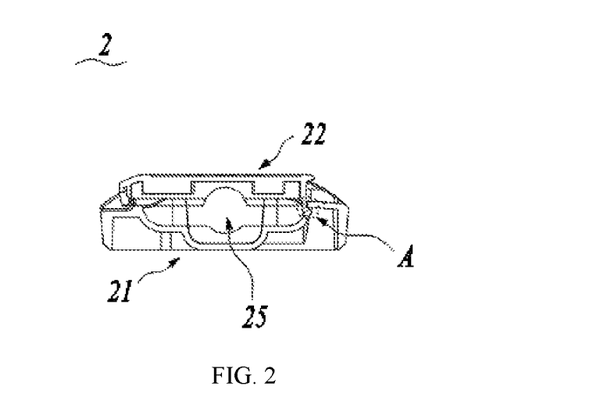
FIG. 2 is a sectional view of an embodiment illustrating the inner package in accordance with the present invention.
Figure 3:
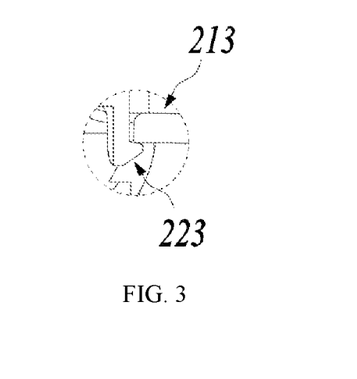
FIG. 3 is a schematic diagram of an enlarged structure of part A circled in FIG. 2.

Referring to FIGS. 1~3, the package is provided with a separate inner package 2, and the inner package 2 comprises a base 21 and a cover 22. The cover 22 is connected to the base 21 in an openable mode, i.e., the first end of the cover 22 is connected to the first side of the base 21, and the second end of the cover 22 is connected to the second side of the base 21 in an assembled mode. When the cover 22 and the base 21 are assembled and closed, the bottom surface of the cover 22 and the base 21 form a holding slot 25 for holding the capsule endoscope 8.

The base 21 can be a plastic base 21, and the holding slot 25 can be directly formed by the upper surface of the base 21 and the cover 22, or the base 21 can comprise a holder 212, and the holder 212 forms the holding slot 25 with the cover 22. The method of connecting the cover 22 to the base 21 is not limited. The first end of the cover 22 may be rotatably connected to the first side of the base 21 by means of pivot connection. The second end of the cover 22 may be connected to the second side of the base 21 by means of snap connection. The extending direction of the holding slot 25 may be cross-perpendicular to the cover 22 or parallel to the length direction of the cover 22.

Therefore, the cover 22 and the base 21 can be connected in an openable mode. When the cover 22 and the base 21 are closed, the cover 22 can form a holding slot 25 with the base 21 to hold the capsule endoscope 8, thus ensuring the reliability of the capsule endoscope 8 during transportation and avoiding the previous squeezing contact that results in overall press and stress on the capsule endoscope 8.

Further, the first end of the cover 22 is pivotally connected to the first side of the base 21.

Further, the second end of the cover 22 is provided with a first snap hook 223, and the second side of the base 21 is provided with a fitted limit portion 213. The first snap hook 223 can fit with the limit portion 213 to connect the cover 22 to the base 21 by means of snap fit.

In the embodiments of the present invention, the cover 22 is configured as a rotating structure with snap hook. Specifically, the first end of the cover 22 is rotatably connected to the first side of the base 21 by means of pivot connection, and the second end of the cover 22 can be assembled and connected with the second side of the base 21 or disconnected from each other. In addition, the second end of the cover 22 can be assembled and connected to the second side of the base 21 in the form of snap connection, wherein the second end of the cover 22 is provided with a first snap hook 223 and the second side of the base 21 is provided with a fitted limit portion 213. By pressing the second end of the cover 22, the first snap hook 223 and the limit portion 213 snap together, thus fixing the cover 22 and the base 21 in a closed state, and forming a holding slot 25 between the cover 22 and the base 21. Also, the first snap hook 223 can be opened so that the first snap hook 223 and the limiting portion 213 are separated from each other for taking out of the capsule endoscope 8.

Further, the bottom surface of the cover 22 is provided with a soft rubber structure 221. When the second end of cover 22 is assembled and connected to the second side of the base 21, the soft rubber structure 221 and the base 21 form the holding slot 25.

Further, the soft rubber structure 221 is an arc-shaped soft rubber structure 221 whose surface shape is adapted to the shape of the outer surface of the capsule endoscope 8, and the arc-shaped soft rubber structure 221 can form a cylindrical holding slot 25 with the base 21.

Further, the inner diameter of the cylindrical holding slot 25 matches the outer diameter of the capsule endoscope 8.

To reduce the impact of damage to the capsule endoscope 8 during transportation or other processes, a soft rubber structure 221 is embedded on the bottom surface of the cover 22, and the soft rubber structure 221 and the base 21 form a holding slot 25. When the capsule endoscope 8 is placed in the holding slot 25, the soft rubber structure 221 can directly contact or interfere with the capsule endoscope 8.

Preferably, the surface of the soft rubber structure 221 can be set in an arc-shaped shape to fit the shape of the outer surface of the capsule endoscope 8. At this time, the arc-shaped soft rubber structure 221 and the base 21 can form a cylindrical holding slot 25. When the arc-shaped soft rubber structure 221 is in contact with the base 21, the contact area of the outer surface of the capsule endoscope 8 receives uniform force, which can effectively alleviate the influence of forces such as friction or squeezing. The top surface of the base 21 can also be recessed to form an arc-shaped surface, so that the cylindrical holding slot 25 is located in the recessed part of the base 21.

Also, the inner diameter of the cylindrical holding slot 25 is set to be the same as or slightly less than the outer diameter of the capsule endoscope 8. In the embodiment, the range of the difference between the inner diameter of the cylindrical holding slot 25 and the outer diameter of the capsule endoscope 8 is 0-0.5 mm. Preferably, the inner diameter of the cylindrical holding slot 25 is 0.2 mm less than the outer diameter of the capsule endoscope 8.

When the inner diameter of the cylindrical holding slot 25 and the outer diameter of the capsule endoscope 8 are the same in size, the arc-shaped soft rubber structure 221 directly contacts the capsule endoscope 8 to limit and fix the capsule endoscope 8.

When the inner diameter of the cylindrical holding slot 25 is slightly less than the outer diameter of the capsule endoscope 8, the arc-shaped soft rubber structure 221 and the capsule endoscope 8 interfere with each other, and a large distributed friction force can be produced to fix the capsule endoscope 8. The arc-shaped soft rubber structure 221 can be arranged in the middle of the cover 22, and the cover 22 is perpendicular to the cylindrical holding slot 25, that is, the arc-shaped soft rubber structure 221 wraps the outer surface of the capsule endoscope 8, and the two interfere with each other. In this case, the radial direction of the capsule endoscope 8 is completely restricted, and it only has degree of freedom in the axial direction, while the cover 22 provides a large enough friction force to make the capsule endoscope 8 be firmly fixed, so as to meet the requirements of reliable fixation.

Further, the base 21 comprises a base body 211 and a holder 212 fixedly connected to the base body 211. When the second end of the cover 22 is assembled and connected to the second side of the base 21, the soft rubber structure 221 and the holder 212 form the holding slot 25.

Specifically, the base 21 comprises a base body 211 and a holder 212, and the holder 212 is fixedly disposed on the base body 211, wherein, the holder 212 may be provided with an arc-shaped recessed portion. When the second end of the cover 22 and the second side of the base 21 are fixed to each other, the arc-shaped recessed portion of the holder 212 forms a holding slot 25 with the soft rubber structure 221 on the cover 22.

The base 21 can be a plastic base, and the holder 212 can be a soft rubber holder. The soft rubber holder 212 is fixedly connected to the plastic base 21 by means of adhesive. After the cover 22 is closed, the soft rubber holder 212 and the soft rubber structure 221 form the holding slot 25. The surface shape of the soft rubber structure 221 is not limited. Preferably, the surface shape of the soft rubber structure 221 can be made to an arc shape, that is, the arc-shaped soft rubber structure 221 and the holder 212 can form a cylindrical holding slot 25.

After the capsule endoscope 8 is placed in the holding slot 25, the soft rubber holder 212 pre-clamps the capsule endoscope 8. Then, under the gravity or squeezing force of the capsule endoscope 8, the force of interference or friction from the soft rubber is moderate and can effectively support and protect the capsule endoscope 8.

Further, the length of the holding slot 25 is not greater than the length of the middle enclosure 82 of the capsule endoscope 8.

Two ends of the capsule endoscope 8 are distributed with camera enclosures, which are untouchable. Only the middle enclosure 82 has no optical requirements and can be used to fix and pick up the capsule endoscope 8.

In order to protect the shooting effect of the camera, the length of the holding slot 25 is restricted, so that only the middle enclosure 82 is in contact with the holding slot 25 after the capsule endoscope 8 is placed in the holding slot 25, and the camera enclosures at two ends protrude out of the holding slot 25 to avoid contact between the camera enclosures and the holding slot 25.

Preferably, the holding slot 25 comprises reserved space for fingers to pinch the capsule endoscope 8, and the reserved space for fingers corresponds to the position of the middle enclosure 82 of the capsule endoscope 8 so as to pinch the middle enclosure 82 of the capsule endoscope 8 for convenient placement when packaging and take out for use.

Figure 4:
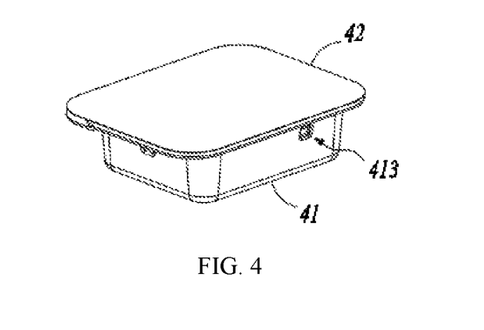
FIG. 4 is a schematic view of an embodiment illustrating a sealing structure in accordance with the present invention.

Further, referring to FIG. 4, the package further comprises a sealing structure 4. The sealing structure 4 comprises a blister case 41 and a dialysis paper 42. The surface of the blister case 41 is recessed to form a first holding chamber 45. The inner package 2 can be fixed in the first holding chamber 45. The dialysis paper 42 can be seamlessly connected to the upper surface edge of the blister case 41 to seal the first holding chamber 45.

After the capsule endoscope 8 is placed in the inner package 2 and fixed therein, a fixed integral structure is formed, the fixed integral structure can be put into the sealing structure 4 for sealing.

Specifically, the package further comprises a sealing structure 4, which comprises a blister case 41 and a dialysis paper 42. The surface of the blister case 41 is recessed to form a first holding chamber 45, and the blister case 41 may also be provided with a concave-convex structure 413. After putting the entire inner package 2 into the first holding chamber 45, the concave-convex structure 413 can limit and fix the entire inner package 2 so that the entire inner package 2 is relatively fixed with the blister case 41. Then, the upper surface edge of the blister case 41 can be connected to the dialysis paper 42 by heat sealing to seal the first holding chamber 45. The dialysis paper 42 has the function of breathing and bacteria isolating, and provides aseptic guarantee for storage of the capsule endoscope 8, that is, the sealed integral structure can be subsequently sterilized as a whole.

The method of fixing the inner package 2 as a whole to the blister case 41 is not limited. Other method such as fixing by adhesive may also be used.

Figure 5:
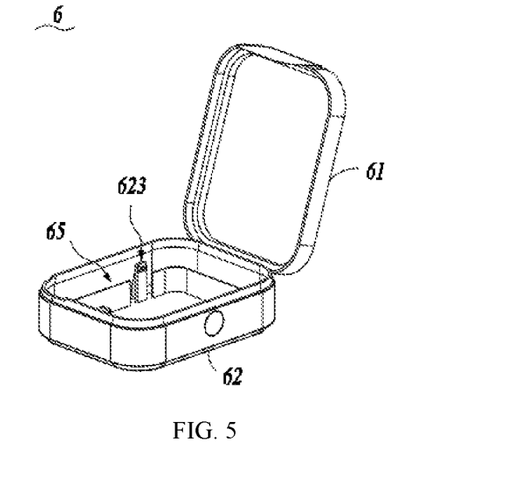
FIG. 5 is a schematic view of an embodiment illustrating an outer package in accordance with the present invention.
Figure 6:
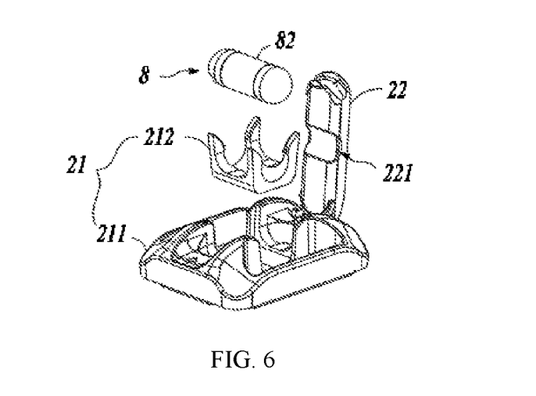
FIG. 6 is an exploded view of an embodiment illustrating the inner package and the capsule endoscope in accordance with the present invention.
Figure 7:
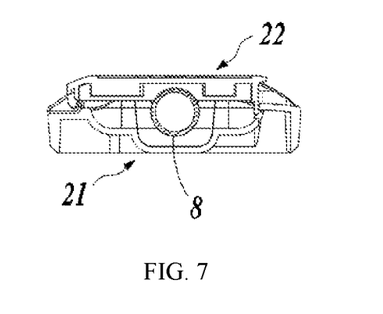
FIG. 7 is a sectional view of an embodiment illustrating the closed inner package in accordance with the present invention.
Figure 8:
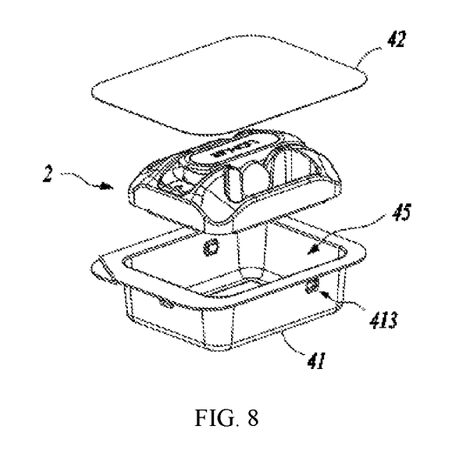
FIG. 8 is an exploded view of an embodiment illustrating a package in accordance with the present invention.
Figure 9:
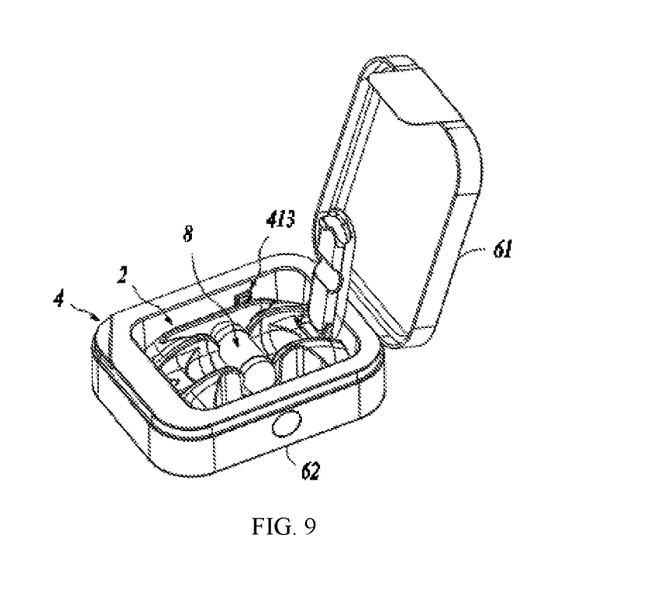
FIG. 9 is a schematic view of an embodiment illustrating the opened package in accordance with the present invention.
Figure 10:
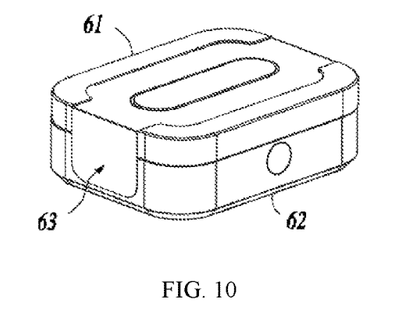
FIG. 10 is a schematic view of an embodiment illustrating the closed package in accordance with the present invention.

Further, the package further comprises an outer package 6. The outer package 6 comprises an upper cover 61 and a lower cover 62 that are detachably connected, and the upper cover 61 and the lower cover 62 form a second holding chamber 65. The sealing structure 4 can be fixed in the second holding chamber 65.

After the capsule endoscope 8 is fixed to the inner package 2, the closed inner package 2 is placed in the sealing structure 4 for overall sterilization or aseptic sealing, and then the sealed and sterilized overall structure is continued to go through outer packaging.

Referring to FIG. 5, the package further comprises an outer package 6 and the outer package 6 comprises an upper cover 61 and a lower cover 62. The second holding chamber 65 is formed between the upper surface of the lower cover 62 and the lower surface of the upper cover 61, which can be formed by recessing the upper surface of the lower cover 62, by recessing the lower surface of the upper cover 61, or by recessing the both.

After the sealing structure 4 is wholly placed into the second holding chamber 65, the upper cover 61 is detachably connected to the lower cover 62, which may be either by connecting the upper cover 61 to at least two sides of the lower cover 62 with a sealing sticker 63, or by connecting the upper cover 61 to the lower cover 62 rotatably and openably by means of a snap hook and a pivot, to facilitate opening or closing.

Preferably, the upper surface of the lower cover 62 is recessed to form a second holding chamber 65 with the upper cover 61, wherein the lower surface of the upper cover 61 may also be recessed. The lower cover 62 may also be provided with a second snap hook 623, which fits the concave and convex structure 413 on the blister case 41, and the two may cooperate to fix the lower cover 62 relative to the blister case 41, thereby fixing the sealed and sterilized overall structure with the lower cover 62. Alternatively, a double-sided tape may be used to adhere the bottom of the blister case 41 to the lower cover 62.

The following is an overall description in conjunction with specific embodiments.

As shown in FIGS. 6 to 10, the package comprises a separate inner package 2, a sealing structure 4, and an outer package 6.

The inner package 2 comprises a base 21 and a cover 22, and the base 21 is constructed of plastic. The base 21 comprises a base body 211 and a holder 212. The holder 212 can be a soft rubber holder. The upper surface of the base body 211 is recessed, the holder 212 is located in the recessed area and is fixed to the base body 211. The holder 212 is designed with corresponding arc-shaped recesses on two sides for placing the capsule endoscope 8, and the other two sides of the holder 212 are provided with reserved space for fingers to take out the capsule endoscope 8. One end of the cover 22 pivotally connected to the base 21, and the other end of the cover 22 is provided with a first snap hook 223 that is connected to the limit portion 213 on the base 21 by means of snap fit. The lower surface of the cover 22 is provided with a soft rubber structure 221, which is parallel to the direction of the reserved space for fingers, and the surface of the soft rubber structure 221 is arc shaped to match the outer surface of the capsule endoscope 8, that is, the surface of the soft rubber structure 221 is the same as the outer surface of the capsule endoscope 8. Thus, the arc-shaped soft rubber structure 221 and the arc-shaped recessed portion of the holder 212 form a cylindrical holding slot 25. Also, the length of the holding slot 25 is smaller than the length of the middle enclosure 82 of the capsule endoscope 8, so that only the middle enclosure 82 of the capsule endoscope 8 is in contact with the holding slot 25 which has no contact with two ends of the capsule endoscope 8 with optical lens.

After the capsule endoscope 8 is put in the inner package 2, the cover 22 is pressed to be fixed to the base 21, so that the arc-shaped soft rubber structure 221 can be in direct contact with the capsule endoscope 8 or interfere with the capsule endoscope 8 so as to fix the capsule endoscope 8 firmly.

The sealing structure 4 comprises a blister case 41 and a dialysis paper 42. The surface of the blister case 41 is recessed to form a first holding chamber 45, and the blister case 41 is provided with a concave-convex structure 413. After the capsule endoscope 8 is fixed in the inner package 2, a fixed whole structure is formed, the fixed whole structure is put into the blister case 41, and the concave-convex structure 413 can press against the upper surface of the fixed whole structure to fix the whole structure relative to the blister case 41. The dialysis paper 42 can be thermally connected to the edges of the upper surface of the blister case 41 to seal the first holding chamber 45 for subsequent overall sterilization.

The outer package 6 comprises an upper cover 61 and a lower cover 62. The upper surface of the lower cover 62 is recessed to form a second holding chamber 65 with the upper cover 61. The lower cover 62 is provided with a second snap hook 623. After the sealed and sterilized whole structure is put into the second holding chamber 65, the second snap hook 623 fits with the concave-convex structure 413 on the blister case 41 to fix the lower cover 62 relative to the sealed and sterilized whole structure. At least two sides of the upper cover 61 and the lower cover 62 are detachably connected to each other by a sealing sticker 63, to finally complete the overall package of the capsule endoscope 8.

Figure 11:
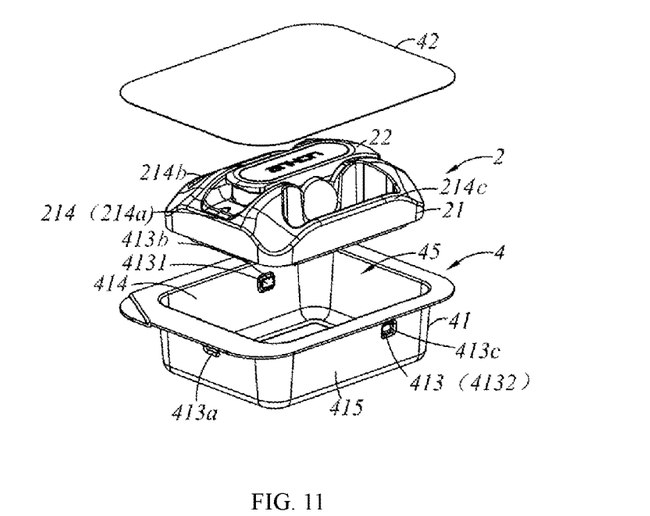
FIG. 11 is a schematic view illustrating the inner package and the sealing structure in an specific example of the present invention.
Figure 12:
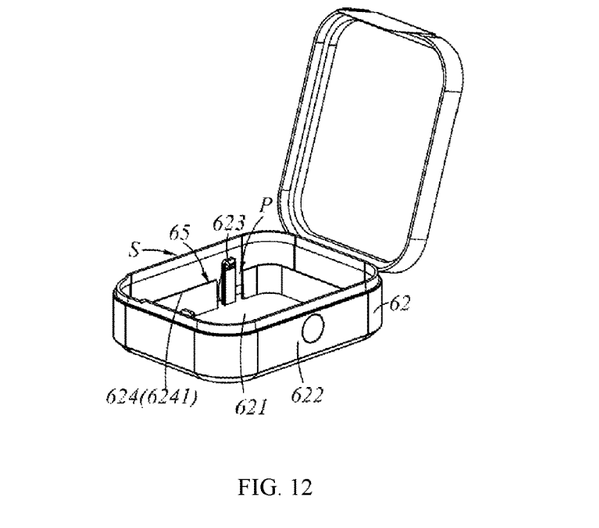
FIG. 12 is a schematic view illustrating the outer package in an specific example of the present invention.
Figure 13:
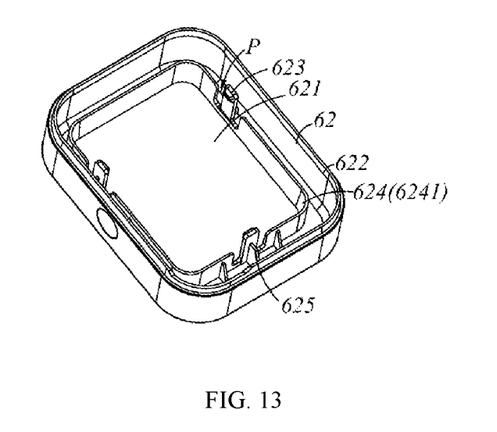
FIG. 13 is a schematic view illustrating the lower cover in an specific example of the present invention.

Referring to FIGS. 11-13, the fitting structure between the inner package 2, the sealing structure 4, and the outer package 6 is described in detail below with a specific example.

The inner package 2 is used to hold the capsule endoscope 8. The sealing structure 4 comprises a blister case 41 and a dialysis paper 42. The surface of the blister case 41 is recessed to form a first holding chamber 45 for accommodating the inner package 2, and the dialysis paper 42 is seamlessly connected to the upper surface edge of the blister case 41 to seal the first holding chamber 45. The outer package 6 is used to hold the sealing structure 4. The inner package 2 comprises a first fitting structure 214, the sealing structure 4 comprises a second fitting structure 413, and the outer package 6 comprises a third fitting structure 623. The second fitting structure 413 is mutually limited with the first fitting structure 214 and the third fitting structure 623 respectively.

Here, the blister case 41 and the dialysis paper 42 fit with each other to form a sealed first holding chamber 45. The dialysis paper 42 is air permeable and can isolate bacteria to provide a sterile guarantee for the storage of the capsule endoscope 8. In addition, the sealing structure 4 is mutually limited with both the inner package 2 and the outer package 6 to improve reliability during transportation and avoid damage to the capsule endoscope.

The inner package 2 comprises a base 21 for holding the capsule endoscope 8. The outer package 6 comprises a lower cover 62, and the lower cover 62 comprises a second holding chamber 65 for holding the sealing structure 4. The first fitting structure 214 comprises a peripheral area of the base 21. The second fitting structure 413 comprises a concave-convex structure 413 located on the blister case 41. The third fitting structure 623 comprises a second snap hook 23 located on the lower cover 62. The concave-convex structure 413 limits the base 21 and the second snap hook 623 limits the concave-convex structure 413.

It can be seen that the inner package 2 and the sealing structure 4 are fixed to each other through the concave-convex structure 413 and the base 21, and the sealing structure 4 and the outer package 6 are fixed to each other through the concave-convex structure 413 and the second hook 623. That is, the arrangement of the concave-convex structure 413 realizes the fixation between the sealing structure 4 and both the inner package 2 and the outer package 6.

Further, the concave-convex structure 413 is located on the side wall 414 of the blister case 41 and protrudes toward the first holding chamber 45. The side of the concave-convex structure 413 facing the first holding chamber 45 is a bracing portion 4131 and the side of the concave-convex structure 413 away from the first holding chamber 45 is a recess 4132. The bracing portion 4131 abuts against the peripheral area of the base 21, and the recess 4132 fits with the second snap hook 623.

Here, the "peripheral area of the base 21" refers to the outermost area as shown in FIG. 11. When viewed from the first holding chamber 45, the concave-convex structure 413 is in the shape of a bump, and the outer surface of the concave-convex structure 413 constitutes the bracing portion 4131. The lower end surface of the bracing portion 4131 abuts against the upper end surface of the peripheral area 214 of the base 21. In this way, the blister case 41 restricts the movement of the base 21 in the vertical direction, and the vertical direction is the superimposed direction of the blister case 41 and the base 21. In addition, the inner surface of the concave-convex structure 413 away from the first holding chamber 45 forms a recess 4132, and the second snap hook 623 is inserted into the recess 4132 to achieve the engagement between the outer package 6 and the sealing structure 4.

Preferably, the concave-convex structure 413 is integrally formed with the blister case 41. In practice, the concave-convex structure 413 can be directly formed by a blister process during the molding of the blister case 41. The concave-convex structure 413 is actually formed by recessing (or projecting) part of the blister case 41.

Specifically, the inner package 2 further comprises a cover 22 arranged above the base 21. The first end of the cover 22 is connected to the first side of the base 21 and the second end of the cover 22 is connected to the second side of the base 21 by means of snap fit. The peripheral area 214 of the base 21 comprises a first periphery 214a set accordingly to the second side of the base 21, and a second periphery 214b and a third periphery 241c connected to the two ends of the first periphery 214a. The concave-convex structure 413 comprises a first concave-convex structure 413a, a second concave-convex structure 413b and a third concave-convex structure 413c arranged correspondingly to the first periphery 214a, the second periphery 214b and the periphery 214c.

Here, "a first periphery 214a set correspondingly to the second side" refers to that the first periphery 214a is set adjacent to the second side. In the embodiment, the first periphery 214a is located at the end of the second side away from the first side. The heights of the periphery 214a, the second periphery 214b and the third periphery 241c are equal. The peripheral area 214 is limited in three directions by the concave-convex structure 413, which can achieve a stable fit between the inner package 2 and the sealing structure 4. In addition, the lower cover 62 comprises three second hooks 623 corresponding to the first concave-convex structure 413a, the second concave-convex structure 413b and the third concave-convex structure 413c.

Further, the lower cover 62 comprises a bottom portion 621 and an outer peripheral portion 622 disposed around the bottom portion 621. The outer peripheral portion 622 comprises an opening S cut in a side away from the bottom portion 621. The second hook 623 is connected to the bottom portion 621 and extends toward the opening S. At this point, the second hook 623 is disposed roughly parallel to the outer peripheral portion 622.

Specifically, the lower cover 62 further comprises an inner peripheral portion 624 connected to the bottom portion 621 and spaced apart from the outer peripheral portion 622. The inner peripheral portion 624 comprises an inner peripheral body 6241 and a second snap hook 623. The inner peripheral portion 624 encloses a second holding chamber 65. When the sealing structure 4 is accommodated in the second holding chamber 65, the inner peripheral body 6241 abuts the outer surface 415 of the blister case 41, and the second snap hook 623 fits with the concave-convex structure 413.

Here, the inner peripheral portion 624 and the outer peripheral portion 622 are roughly parallel to each other. The inner peripheral portion 624 is located inside the outer peripheral portion 622, and the inner peripheral portion 624 fits with the blister case 41, specifically the inner peripheral body 6241 fits with the outer side surface 415 of the blister case 41. Also, the second hook 623 fits with the concave-convex structure 413 at the side wall 414 of the blister case 41. The inner peripheral body 6241 and the second snap hook 623 simultaneously limit the blister case 41, so as to greatly improve the limit effect.

A gap P exists between the second snap hook 623 and the inner peripheral body 6241, and the existence of the gap P can help the second snap hook 623 to be slightly deformed to be snapped into the concave-convex structure 413.

In this case, the bottom end of the second snap hook 623 is interconnected with the bottom end of the inner peripheral body 6241, and a gap P exists between the two sides of the upper end of the second snap hook 623 and their adjacent inner peripheral body 6241, so that the deformation of the second snap hook 623 can be guaranteed while ensuring the overall strength of the inner peripheral portion 624.

Further, the second snap hook 623 protrudes from the inner peripheral body 6241 toward the opening S, and the upper end surface of the outer peripheral portion 622 is farther away from the bottom portion 621 than the upper end surface of the inner peripheral body 6241.

That is, in the vertical direction, the height of the inner peripheral body 6241 is smaller than the height of the second hook 623, while the height of the inner peripheral body 6241 is smaller than the height of the outer peripheral portion 622, which can be adapted to the sealing structure 4.

In addition, the lower cover 62 further comprises a reinforcing portion 625 disposed between the inner peripheral portion 624 and the outer peripheral portion 622. The reinforcing portion 625 at least holds the second snap hook 623. The arrangement of the reinforcing portion 625 can effectively strengthen the second hook 623, thereby improving the limit effect of the second hook 623 on the blister case 41.

The reinforcing portion 625 is a reinforcing rib structure, and is disposed corresponding to the three second hooks 623.

In summary, the disclosed package for the capsule endoscope has a separate inner package 2, which comprises a base 21 and a cover 22 connected to the base 21, wherein the cover 22 is openably connected to the base 21, the cover 22 and the base 21 form a holding slot 25 for placing the capsule endoscope 8, so that the reliability of transportation of the capsule endoscope 8 is improved.

It should be appreciated that even though numerous characteristics and advantages of preferred and exemplary embodiments have been set out in the foregoing description, together with details of the structures and functions of the embodiments, the disclosure is illustrative only. That changes may be made in detail within the principles of the present disclosure to the full extent indicated by the broadest general meaning of the terms in which the appended claims are expressed.

The series of detailed descriptions listed above are only specific descriptions of feasible implementations of the present invention, and are not intended to limit the scope of protection of the present invention. Any equivalent implementations made without departing from the technical spirit of the present invention. The method or change shall be comprised in the protection scope of the present invention.

What is claimed is:
1. A package for a capsule endoscope, comprising
an inner package, wherein
the inner package comprises a base and a cover arranged above the base, a first end of the cover is connected to a first side of the base and a second end of the cover is connected to a second side of the base in an assembled mode;

wherein a bottom surface of the cover comprises a soft rubber structure, and the base comprises a holder, provided an arc-shaped recessed member; the soft rubber structure is an arc-shaped structure, whose surface shape is configured to adapt to a contour of an outer surface of the capsule endoscope, and the arc-shaped soft rubber structure of the cover and the arc-shaped recessed member of the base are configured to form a cylindrical holding slot when the second end of the cover is assembled and connected to the second side of the base;

an inner diameter of the formed cylindrical holding slot is less than or equal to an outer diameter of the capsule endoscope, wherein the inner diameter of the cylindrical holding slot is defined as a diameter of a cross-section of the formed cylindrical holding slot, said cross section is perpendicular to a longitudinal direction of the capsule endoscope which is configured to hold; the soft rubber structure of the cover is configured to directly contact with the capsule endoscope and restrict its movement, reducing an impact of damage to the capsule endoscope during transportation;

the holder of the base, is configured to pre-clamp the capsule endoscope along its longitude direction, so that under gravity or squeezing force of the capsule endoscope, a force of interference or friction from the holder of the base can support and protect the capsule;

the package further comprises a sealing structure comprising a blister case and a dialysis paper, wherein the surface of the blister case is recessed to form a first holding chamber, the inner package is fixed in the first holding chamber, and the dialysis paper is seamlessly connected to the upper surface edge of the blister case to seal the first holding chamber; and an outer package, wherein the outer package comprises an upper cover and a lower cover that are detachably connected, and the upper cover and the lower cover form a second holding chamber; a sealing structure is fixed in the second holding chamber.

2. The package of claim 1, wherein the first end of the cover is pivotally connected to the first side of the base.

3. The package of claim 2, wherein the second end of the cover comprises a first snap hook, and the second side of the base comprises a fitted limit portion, wherein the first snap hook fits with the limit portion to connect the cover to the base by means of snap fit.

4. The package of claim 1, wherein the base comprises a base body and the holder is fixedly connected to the base body.

5. The package of claim 1, wherein the length of the cylindrical holding slot is not greater than the length of the middle enclosure of the capsule endoscope.

6. The package of claim 1, wherein the package further comprises a sealing structure and an outer package, and the sealing structure comprises a blister case and a dialysis paper, the surface of the blister case is recessed to form a first holding chamber for accommodating the inner package, the dialysis paper is seamlessly connected to the upper surface edge of the blister case to seal the first holding chamber, and the outer package holds the sealing structure, the inner package comprises a first fitting structure, the sealing structure comprises a second fitting structure, the outer package comprises a third fitting structure, and the second fitting structure is mutually limited with the first fitting structure and the third fitting structure respectively.

7. The package of claim 6, wherein the outer package comprises a lower cover, the lower cover comprises a second holding chamber for accommodating the sealing structure, and the first fitting structure comprises a peripheral area of the base, the second fitting structure comprises a concave-convex structure located on the blister case, and the third fitting structure comprises a second snap hook located on the lower cover, wherein the concave-convex structure limits the base and the second hook limits the concave-convex structure.

8. The package of claim 7, wherein the concave-convex structure is located on the side wall of the blister case and protrudes toward the first holding chamber, and the side of the concave-convex structure facing the first holding chamber is a bracing portion, the side of the concave-convex structure away from the first holding chamber is a recess, the bracing portion abuts against the peripheral area of the base, and the recess fits with the second snap hook.

9. The package of claim 7, wherein the peripheral area of the base comprises a first periphery set accordingly to the second side of the base, and a second periphery and a third periphery connected to the two ends of the first periphery, the concave-convex structure comprises a first concave-convex structure, a second concave-convex structure and a third concave-convex structure arranged correspondingly to the first periphery, the second periphery and the periphery.

10. The package of claim 8, wherein the concave-convex structure is integrally formed with the blister case.

11. The package of claim 7, wherein the lower cover comprises a bottom portion and an outer peripheral portion disposed around the bottom portion, and the outer peripheral portion comprises an opening cut in a side away from the bottom portion, the second hook is connected to the bottom portion and extends toward the opening.

12. The package of claim 11, wherein the lower cover further comprises an inner peripheral portion connected to the bottom portion and spaced apart from the outer peripheral portion, the inner peripheral portion comprises an inner peripheral body and a second snap hook, the inner peripheral portion encloses a second holding chamber, the inner peripheral body abuts the outer surface of the blister case and the second snap hook fits with the concave-convex structure when the sealing structure is accommodated in the second holding chamber.

13. The package of claim 12, wherein a gap exists between the second snap hook and the inner peripheral body, the lower cover further comprises a reinforcing portion disposed between the inner peripheral portion and the outer peripheral portion, and the reinforcing portion at least holds the second snap hook.

14. The package of claim 12, wherein the second snap hook protrudes from the inner peripheral body toward the opening, and the upper end surface of the outer peripheral portion is away from the bottom portion.

15. The package of claim 7, wherein the outer package further comprises an upper cover detachably connected to the lower cover, and the upper cover and the lower cover form a second holding chamber.

* * * * *